(12) United States Patent
Miller

(10) Patent No.: US 7,230,208 B2
(45) Date of Patent: Jun. 12, 2007

(54) OVEN FOR DENTAL PROSTHESES OR PARTIAL DENTAL PROSTHESES

(75) Inventor: Stephan Miller, Traunstein (DE)

(73) Assignee: Dekema Dental-Keramiköfen GmbH (DE)

(*) Notice: Subject to any disclaimer, the term of this patent is extended or adjusted under 35 U.S.C. 154(b) by 10 days.

(21) Appl. No.: 10/558,466

(22) PCT Filed: May 27, 2004

(86) PCT No.: PCT/EP2004/005722

§ 371 (c)(1),
(2), (4) Date: Nov. 28, 2005

(87) PCT Pub. No.: WO2004/106829

PCT Pub. Date: Dec. 9, 2004

(65) Prior Publication Data

US 2007/0029304 A1  Feb. 8, 2007

(30) Foreign Application Priority Data

May 28, 2003  (DE) .......................... 203 08 406 U

(51) Int. Cl.
  F27B 5/14  (2006.01)
  F27B 17/02 (2006.01)
  H05B 3/46  (2006.01)
  H05B 3/66  (2006.01)

(52) U.S. Cl. .................... 219/409; 219/402; 219/408; 219/548; 433/32; 373/134

(58) Field of Classification Search ................ None
See application file for complete search history.

(56) References Cited

U.S. PATENT DOCUMENTS

| 1,959,358 | A | * | 5/1934 | Gouverneur | 219/406 |
| 5,432,319 | A | | 7/1995 | Indig | |
| 6,252,202 | B1 | * | 6/2001 | Zychek | 219/390 |
| 6,386,265 | B1 | | 5/2002 | Usui | |
| 6,441,346 | B1 | * | 8/2002 | Zychek | 219/411 |

FOREIGN PATENT DOCUMENTS

DE  197 53 895 A  6/1999
GB     334 963 A  9/1930

* cited by examiner

*Primary Examiner*—Joseph Pelham
(74) *Attorney, Agent, or Firm*—Harness, Dickey & Pierce, P.L.C.

(57) ABSTRACT

The invention relates to a stove for producing denture and or the parts thereof comprising a combustion chamber and a heating device which is arranged therein and provided with a heating spiral consisting of an appropriate resistance wire and a support for the heating spiral. The aim of said invention is to better use the heating energy and make it possible to easily replace the heating device. For this purpose, the heating spiral is arranged on the external part of the support.

10 Claims, 4 Drawing Sheets

OVEN FOR DENTAL PROSTHESES OR PARTIAL DENTAL PROSTHESES

CROSS-REFERENCE TO RELATED APPLICATIONS

This application is a National Stage of International Application No. PCT/EP2004/005722, filed May 27, 2004, and which claims priority to German Patent Application No. 203 08 406.3, filed May 28, 2003. The disclosures of these applications are incorporated herein by reference.

FIELD AND BACKGROUND OF THE INVENTION

The present invention relates to an oven for dental prostheses or partial dental prostheses comprising a firing chamber and a heating device arranged in the firing chamber and having a heating filament formed from a suitable heating wire and a carrier for the heating filament.

With known ovens of the named kind, a tubular glass filament guided around at the inner side of the firing chamber is used and a likewise coiled heating wire is arranged in it. The heating filament has good guidance and protection in this manner. The heating device can also be replaced simply and no direct energy transfer to the walls of the firing chamber takes place.

It is disadvantageous with a heating device of this type, however, that the carrier filament has to be manufactured of quartz glass since the ovens are also operated with underpressure in the firing chamber so that essentially only the radiant heat is available. However, some of the radiation is also absorbed on the use of quartz glass. The quartz glass can additionally fog up or even become dull.

In other ovens for dental prostheses or partial dental prostheses, the heating filament is embedded in the walls of the firing chamber. Since the coefficient of expansion of the heating filament and of the wall material differ from one another, there is the risk that the wall material will crack. Furthermore, the embedded heating filament also emits energy directly to the walls in a substantial degree so that strong heat losses arise. A further disadvantage consists of the fact that the radiation of the embedded parts of the heating filament cannot be used. Finally, the exchange of the heating device is also difficult since the heating filament can only be replaced, if at all, together with the embedding mass.

SUMMARY OF THE INVENTION

It is the underlying object of the invention to provide an oven of the initially named kind which does not have these disadvantages. It should in particular be equipped with a heating device which makes possible a good utilization of the radiant heat, is simple to replace and loses as little energy as possible to the firing chamber walls and/or the carrier metal.

This object is satisfied in that the heating filament is arranged outwardly on the carrier.

The heating filament is exposed by the arrangement of the heating filament outwardly on the carrier so that the whole radiation spectrum can be used. The heating device is nevertheless easily replaceable since the heating filament can be removed together with the carrier. Further advantages consist of the fact that no direct transfer of energy to the insulation of the firing chamber takes place; that other heat-resistant materials can also be used as carriers, even those which have a higher heat resistance than quartz glass; and that existing heating devices with a heating filament arranged in a carrier can be replaced with the new heating device.

All correspondingly temperature-resistant and sufficiently stable materials can be considered as carriers.

The carrier for the heating filament can consist of glass, for example. If quartz glass is used, the radiation of the turns of the heating filament disposed on the rear side of the heating filament can also be utilized.

Ceramic materials can also be used as the carrier material, in particular highly heat resistant ceramics such as aluminum oxide or zirconium oxide. Work can thereby be carried out at particularly high temperatures.

In accordance with a preferred embodiment of the invention, the carrier is made in tubular form. The carrier structure is thus more stable, material is saved and the mass of inertia and the energy absorbance of the carrier are reduced.

To heat the firing chamber as ideally as possible, the carrier with the heating filament is itself coiled. It can thereby be arranged at the inside of the firing chamber walls and surround the firing space from all sides.

In accordance with a further embodiment of the invention, the carrier is longer than the heating filament, in particular by approximately one turn. The additional turn can serve to support the carrier with the heating filament on the base of the firing chamber.

The diameter of the additional turn of the carrier is preferably larger than its other turns. A spacing is thereby ensured in a simple manner between the heating filament and the walls of the firing chamber and so a direct heating of the firing chamber walls is prevented.

To prevent the heating filament from slipping on the carrier, it is preferably provided with holding means. The carrier can, for example, have a kink.

Another possibility of supporting the heating device in the firing chamber consists of making an end of the carrier angled and of inserting a corresponding recess in the base of the firing chamber. A stable structure can thus also be achieved.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
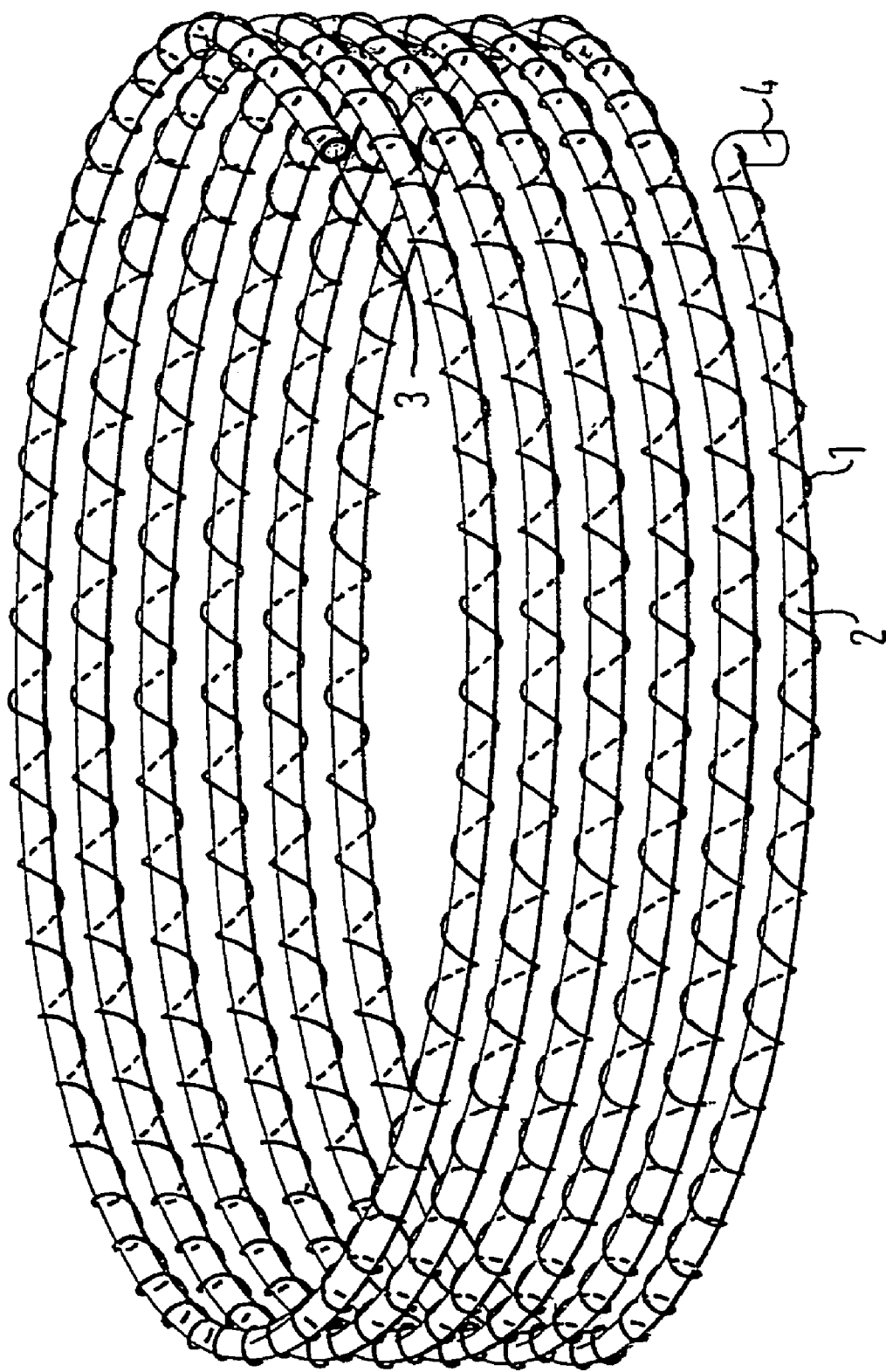
FIG. 1 schematically illustrates a first heating filament with carrier in accordance with the invention.

FIG. 1 shows a heating filament 1 made of a suitable heating wire which has a plurality of turns and is arranged on a glass rube 2 as a carrier. The glass tube 2 is likewise made as a coil and has six turns arranged over one another. The heating filament 1 is correspondingly also formed with the glass tube 2 with six large turns.

Figure 2:
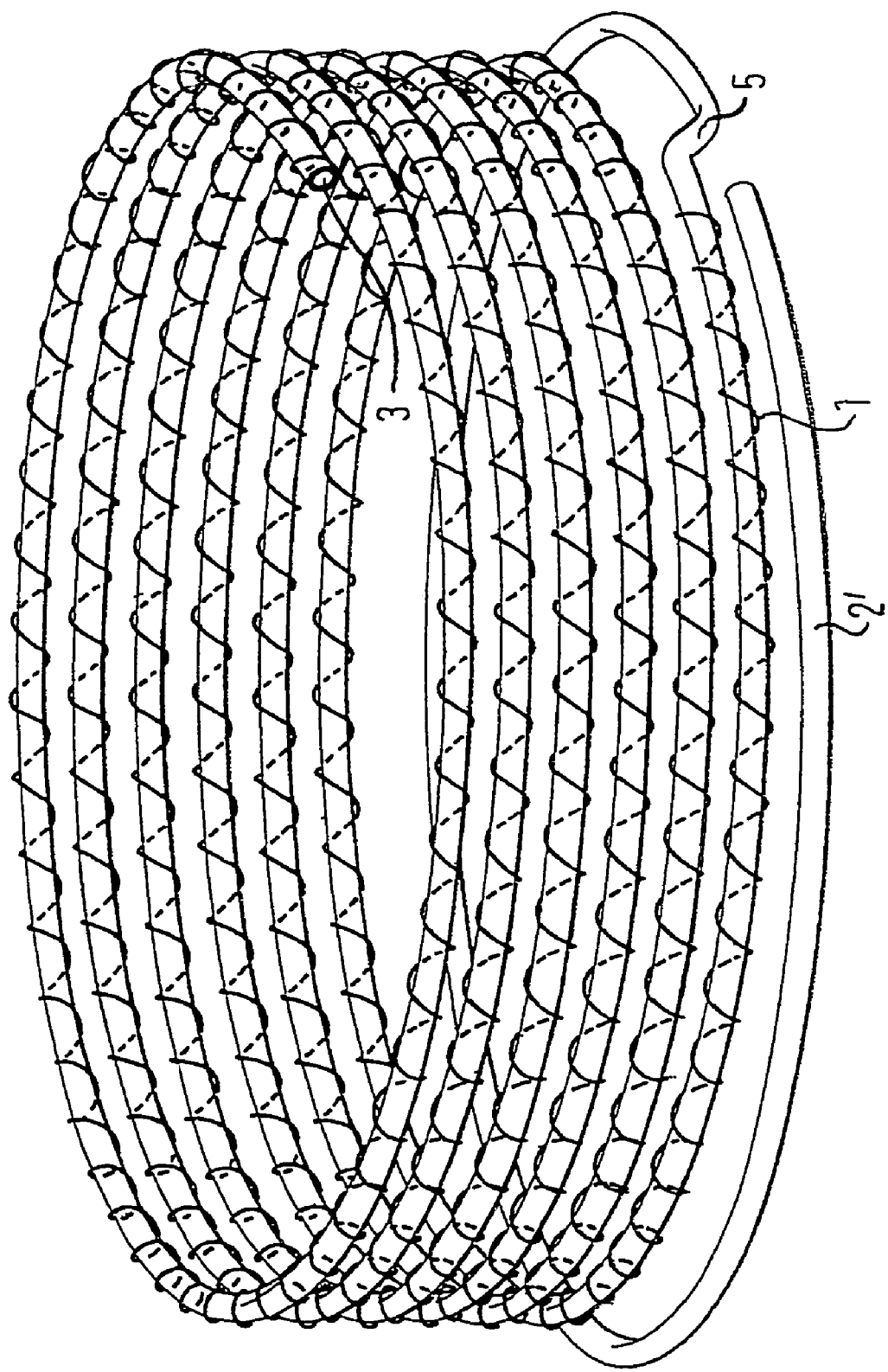
FIG. 2 schematically illustrates a second heating filament with carrier in accordance with the invention.

The upper end 3 of the glass tube 2 is straight, whereas the lower end 4 is angled. The angled end 4 of the gas tube 2, on the one hand, prevents a slipping of the heating filament 1 on the glass tube 2 and, on the other hand, serves for the fastening of the glass tube 2 in the firing chamber not shown here. For this purpose, the firing chamber has a corresponding recess in its base into which the angled end 4 of the glass tube 2 is inserted. Instead of the angled end 4, the glass tube 2 can, as shown in FIG. 2, also be provided with an additional turn which is also supported on the base of the firing chamber. The additional turn has a larger diameter than the other turns in order to ensure a spacing of the heating filament 1 from the walls of the firing chamber. The glass tube 2' is also provided in this case with a kink 5 to prevent a slipping of the heating filament 1 on the glass tube 2'.

Quartz glass or also normal glass can also be used as the glass. A different heat-resistant material can also be used, for example a ceramic material. It is important that the carrier material can be used in the corresponding temperature range and has sufficient stability.

Figure 3:
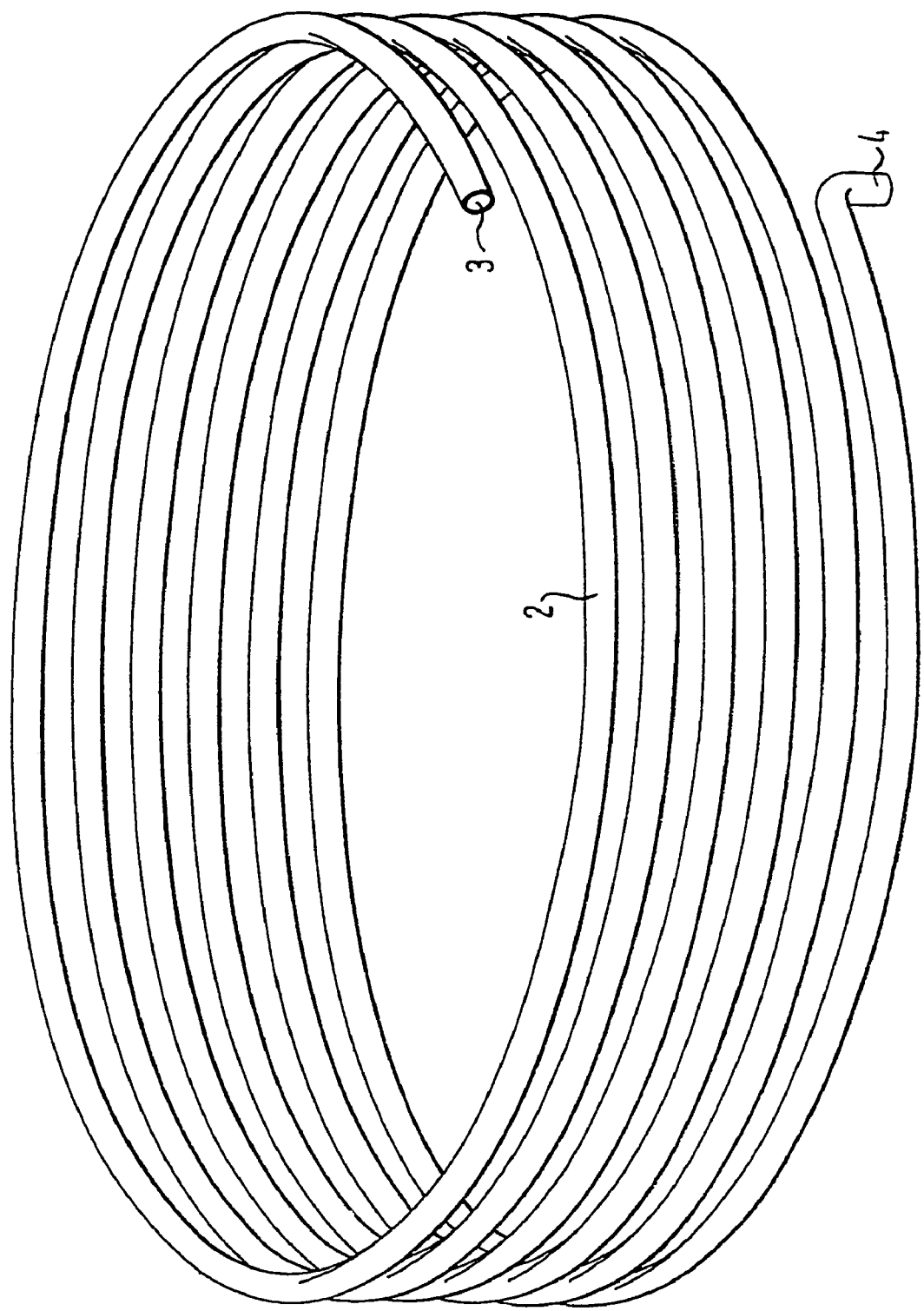
FIG. 3 schematically illustrates the carrier of FIG. 1 without a heating filament.
Figure 4:
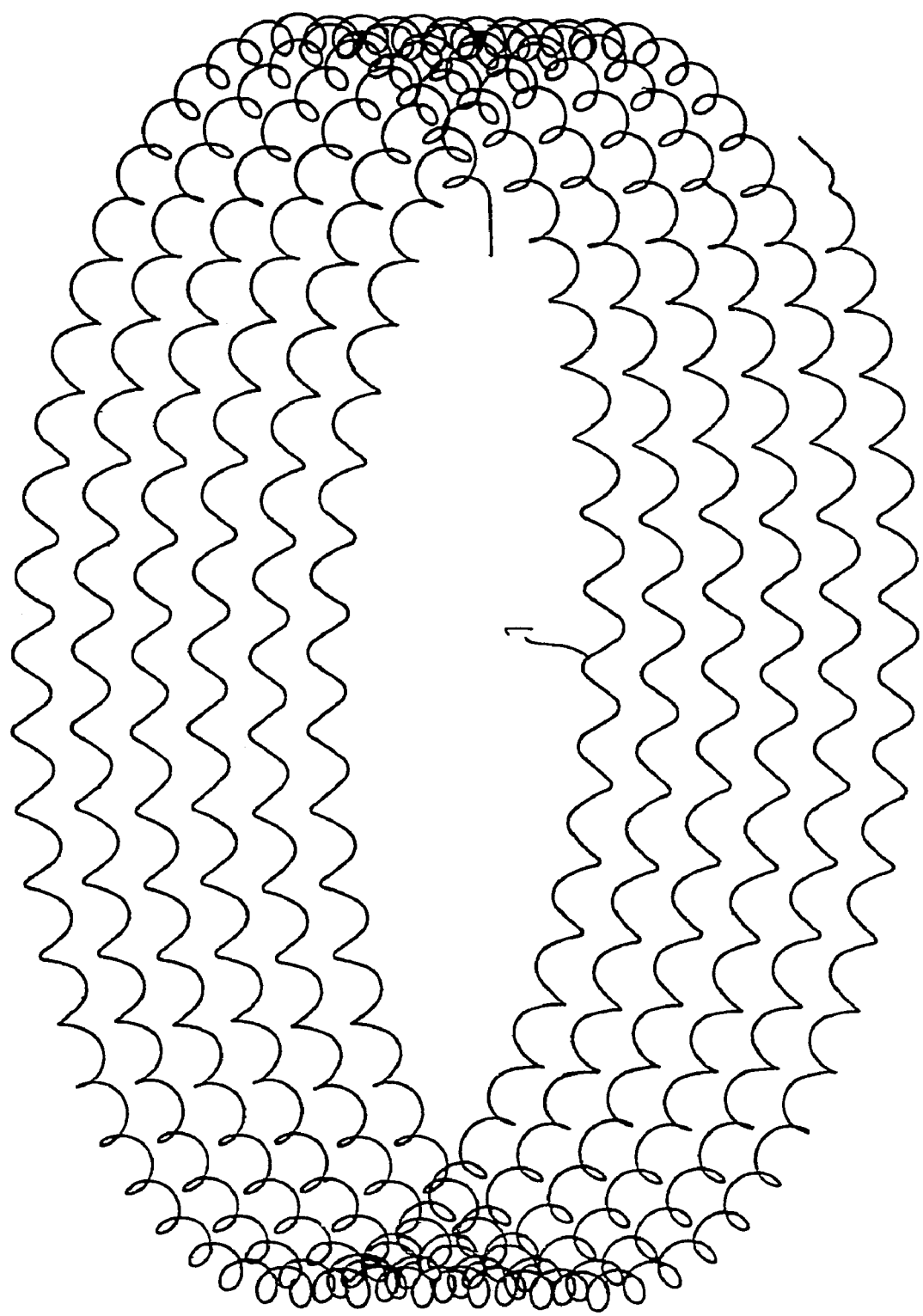
FIG. 4 schematically illustrates the heating filament of FIG. 1 and FIG. 2 without a carrier.

The manufacture of an oven in accordance with the invention having the heating device shown in FIG. 1 can take place, for example, such that a glass tube 2 is formed as a filament in the manner shown in FIG. 3. Furthermore, a heating filament 1 is formed in the manner shown in FIG. 4 with a plurality of small turns with a corresponding number of large turns. The glass tube 2 is then introduced into the hollow core of the heating filament 1 until the heating filament abuts the angled end 4 of the glass tube 2. The glass tube 2 with the heating filament 1 is subsequently inserted into the firing chamber and anchored in the base of the firing chamber via the angled end 4.

The manufacture of an oven having the heating device shown in FIG. 2 takes place accordingly, with the heating filament abutting the kink 5 of the glass tube 2' and the bottommost turn of the same with the enlarged diameter providing a fixing of the heating device in the firing chamber.

The description of the invention is merely exemplary in nature and, thus, variations that do not depart from the gist of the invention are intended to be within the scope of the invention. Such variations are not to be regarded as a departure from the spirit and scope of the invention.

REFERENCE NUMERAL LIST 1 heating filament
2, 2' glass tube
3 straight end of 2
4 angled end of 2
5 kink in 2'

The invention claimed is:

1. An oven for dental prostheses or partial dental prostheses comprising a firing chamber and a heating device arranged in the firing chamber and having a heating filament formed from a heating wire and a helically shaped carrier for the heating filament,
wherein
the heating filament is wound outwardly around the turns of the carrier.

2. An oven in accordance with claim 1, wherein the carrier consists of glass.

3. An oven in accordance with claim 1, wherein the carrier consists of quartz glass.

4. An oven in accordance with claim 1, wherein the carrier consists of a ceramic material.

5. An oven in accordance with claim 1, wherein the carrier is tubular.

6. An oven in accordance with claim 1, wherein the carrier is longer than the heating filament, in particular by approximately one turn.

7. An oven in accordance with claim 6, wherein at the diameter of the additional turn of the carrier is larger than its other turns.

8. An oven in accordance with claim 1, wherein the carrier is provided with holding means to prevent a slipping of the heating filament with respect to the carrier.

9. An oven in accordance with claim 1, wherein one end of the carrier is angled and is inserted into a corresponding recess in the base of the firing chamber.

10. An oven in accordance with claim 1, wherein the carrier is itself coil formed with the heating filament.

* * * * *